(12) United States Patent
Matheis et al.

(10) Patent No.: US 8,419,671 B2
(45) Date of Patent: Apr. 16, 2013

(54) APPLIANCE FOR CANNULATION OF A BLOOD VESSEL

(75) Inventors: Georg Matheis, Burladingen (DE); Heiko Frerichs, Hechingen (DE); Axel Sandmann, Oberried (DE); Dietmar Klietsch, Herrenberg (DE)

(73) Assignee: Novalung GmbH, Talheim (DE)

( * ) Notice: Subject to any disclaimer, the term of this patent is extended or adjusted under 35 U.S.C. 154(b) by 153 days.

(21) Appl. No.: 12/416,847

(22) Filed: Apr. 1, 2009

(65) Prior Publication Data

US 2009/0187133 A1   Jul. 23, 2009

Related U.S. Application Data

(62) Division of application No. 10/742,452, filed on Dec. 19, 2003, now abandoned.

(30) Foreign Application Priority Data

Dec. 23, 2002   (DE) .................................. 102 61 575

(51) Int. Cl.
 *A61M 37/00*   (2006.01)
(52) U.S. Cl.
 USPC ....... 604/4.01; 604/6.1; 604/6.14; 604/96.01; 604/103.07
(58) Field of Classification Search ............... 604/4.01, 604/6.1, 6.14, 96.01, 103.07
 See application file for complete search history.

(56) References Cited

U.S. PATENT DOCUMENTS

| | | | |
|---|---|---|---|
| 4,581,017 A | 4/1986 | Sahota | |
| 4,850,954 A | 7/1989 | Charvin | |
| 5,009,636 A | 4/1991 | Wortley et al. | |
| 5,224,938 A * | 7/1993 | Fenton, Jr. | 604/247 |
| 5,295,995 A | 3/1994 | Kleiman | |
| 5,334,142 A | 8/1994 | Paradis | |
| 5,470,314 A | 11/1995 | Walinsky | |
| 5,649,941 A * | 7/1997 | Lary | 606/159 |
| 5,746,709 A | 5/1998 | Rom et al. | |
| 5,759,172 A * | 6/1998 | Weber et al. | 604/103.07 |
| 5,766,151 A | 6/1998 | Valley et al. | |
| 5,947,924 A | 9/1999 | Liprie | |
| 6,120,494 A | 9/2000 | Jonkman | |

(Continued)

FOREIGN PATENT DOCUMENTS

| | | |
|---|---|---|
| DE | 19515933 | 11/1996 |
| DE | 19622184 | 12/1997 |

(Continued)

OTHER PUBLICATIONS

Office Action from Cattaneo et al., U.S. Appl. No. 11/897,667, dated Mar. 9, 2009, (8 pages).

(Continued)

*Primary Examiner* — Leslie Deak
(74) *Attorney, Agent, or Firm* — Seed IP Law Group PLLC

(57) ABSTRACT

The present invention relates to an appliance for cannulation of a blood vessel with a cannula which, after introduction into the vessel, is in fluidic communication with the vessel. At least one means is also provided to permit a controlled division of the blood into a first subsidiary stream which leaves the vessel through the cannula, and a second subsidiary stream which continues to flow through the vessel.

31 Claims, 5 Drawing Sheets

U.S. PATENT DOCUMENTS

| | | | |
|---|---|---|---|
| 6,165,163 | A | 12/2000 | Chien et al. |
| 6,270,490 | B1 | 8/2001 | Hahnen |
| 6,296,654 | B1 | 10/2001 | Ward |
| 6,387,037 | B1 | 5/2002 | Bolling et al. |
| 6,390,969 | B1 | 5/2002 | Bolling et al. |
| 6,613,038 | B2 | 9/2003 | Bonutti et al. |
| 6,673,042 | B1 | 1/2004 | Samson et al. |
| 6,679,871 | B2 | 1/2004 | Hahnen |
| 2001/0001812 | A1 | 5/2001 | Valley et al. |
| 2002/0186166 | A1 | 12/2002 | Viole et al. |
| 2002/0188166 | A1 | 12/2002 | Viole et al. |
| 2003/0135152 | A1 | 7/2003 | Kollar et al. |
| 2004/0082906 | A1 | 4/2004 | Tallarida et al. |
| 2005/0027245 | A1 | 2/2005 | Sachdeva et al. |
| 2005/0038408 | A1 | 2/2005 | von Segesser |
| 2005/0107820 | A1 | 5/2005 | Forsberg et al. |
| 2006/0036218 | A1 | 2/2006 | Goodson, IV et al. |
| 2006/0167405 | A1 | 7/2006 | King et al. |
| 2008/0188806 | A1 | 8/2008 | Cattaneo et al. |
| 2009/0187133 | A1 | 7/2009 | Matheis et al. |

FOREIGN PATENT DOCUMENTS

| | | |
|---|---|---|
| DE | 10006825 | 9/2001 |
| EP | 0 301 854 | 2/1989 |
| EP | 0301854 | 2/1989 |
| FR | 2 220 283 | 10/1974 |
| FR | 2220283 | 10/1974 |
| JP | 58-103977 | 1/1985 |
| JP | 61-1193670 | 8/1986 |
| JP | 06-233823 | 6/1994 |
| JP | 07-504595 | 5/1995 |
| JP | 2001-518325 | 10/2001 |
| JP | 03-103123 | 4/2003 |
| WO | WO94/00178 | 1/1994 |
| WO | WO 94/00178 | 1/1994 |
| WO | WO2005/002454 | 1/2005 |
| WO | WO 2005/002454 | 1/2005 |

OTHER PUBLICATIONS

Office Action from Cattaneo et al., U.S. Appl. No. 11/897,567, dated Nov. 13, 2009, (6 pages).

Office Action from Cattaneo et al., U.S. Appl. No. 11/897,567, dated May 26, 2010, (7 pages).

Office Action from Cattaneo et al., U.S. Appl. No. 11/897,567, dated May 26, 2011, (7 pages).

Kasirajan, et al. "Technique to Prevent Limb Ischemia during Peripheral Cannulation for Extracorporeal Membrane Oxygenation" Perfusion 17:427-428, 2002.

Reng, et al. "Pumpless Extracorporeal Lung Assist and Adult Respiratory Distress Syndrome" The Lancet, 356:219-220, 2000.

Salm, et al. "Prevention of Lower Extremity Ischemia During Cardiopulmonary Bypass via Femoral Cannulation" Ann. Thorac. Surg. 63:251-252, 1997.

Wimmer-Greinecker, et al. "Complications of Port-Access Cardiac Surgery" J. Card. Surg. 14:240-245, 1999.

\* cited by examiner

APPLIANCE FOR CANNULATION OF A BLOOD VESSEL

CROSS-REFERENCE TO RELATED APPLICATIONS

This application is a divisional of application Ser. No. 10/742,452, filed Dec. 19, 2003, which claims the benefit of German Patent Application No. DE 102 61 575.6, filed Dec. 23, 2002.

FIELD OF THE INVENTION

The present invention relates to an appliance for cannulation of a blood vessel with a cannula which, after introduction into the vessel, is in fluidic communication with the vessel, and also to the use of the appliance and to a method for cannulation of blood vessels.

DESCRIPTION OF THE RELATED ART

Such appliances are already known in the medical field and are used in many different medical indications.

For example, they are used in extracorporeal blood circuits, for example for extracorporeal lung assist. This is necessary when a patient's pulmonary function is impaired and the body's oxygen supply is at risk. In this connection, apparatuses have now been used for some time which, like a heart-lung machine in open-heart surgery, can temporarily take over the function of the diseased lung.

In temporary extracorporeal lung assist (ECLA), extracorporeal membrane oxygenation (ECMO) has for many years been an established treatment procedure in patients with acute severe lung failure. As with the heart-lung machine, blood is removed from one of the large vena cava, for example, via a wide-lumen cannula, is driven through membrane lungs in the extracorporeal system by means of a pump, and is then returned via a second cannula which is positioned, for example, in the aorta.

In patients with good haemodynamic parameters, it is even possible to create an arterio-venous shunt which allows a lung assist device with low resistance to be used without pump. This interventional lung assist (ILA) allows the gas exchange of the lungs to be assisted extracorporeally, without use of machines, via a lung assist device designed as a disposable product (see, for example, Reng et al. "Pumpless extracorporeal lung assist and adult respiratory distress syndrome", 2000, The Lancet 356: 219-220).

In the prior art, vessels are cannulated using cannulas whose size or diameter is chosen in particular with reference to the size of the femoral artery.

The cannula size is chosen in such a way that the area of the lower extremity beyond the cannula is still supplied with blood.

However, as a result of the overall trauma triggered, for example, by high doses of medication, blood transfusions, septic reactions, etc., there may be severe contractions of the arteries in particular. With these contractions, the diameter of the vessels becomes narrower, as a result of which the femoral artery closes tightly around the arterial cannula. In this way, all of the blood guided in the artery flows into the cannula and, via the cannula, into the femoral vein of the other leg, which means that blood supply to the distal areas of the leg with the arterial cannula is no longer guaranteed. As a result of this undersupply of arterial, oxygen-enriched blood, tissue necrosis takes place below the cannulation site unless the depleted blood flow is detected and treated in good time.

In the prior art, various attempts have been made to prevent these complications. Thus, in "Technique to prevent limb ischemia during peripheral cannulation for extracorporeal membrane oxygenation", Perfusion 17: 427-428 (2002), Kasirajan et al. briefly describe a method in which, in order to prevent ischaemia, arterial reperfusion with concurrent distal venous drainage is applied. To do this, two cannulas of different sizes are fitted in each case into the femoral artery and into the femoral vein, and the arterial and venous cannulas are in each case connected to one another in a Y shape.

Moreover, in the publication entitled "Prevention of Lower Extremity Ischemia during Cardiopulmonary Bypass via Femoral Cannulation", Ann. Thorac. Surg. 63: 251-252 (1997), Salm describes a technique for preventing ischaemia of the lower extremities in which perfusion of the femoral artery is achieved using a stent whose end is sutured laterally onto the artery.

However, these techniques have the disadvantages that the insertion of the two further cannulas additionally damages and thus irritates the vessels. Moreover, the method is made very complicated by the use of four cannulas.

For general cannulation of vessels, the prior art also includes balloon catheters with which vessels can be closed.

Wimmer-Greinecker et al., in "Complications of Port-Access Cardiac Surgery", J. Card. Surg. 14: 240-245 (1999), describe cannulation of the femoral artery and vein in connection with a cardiopulmonary bypass, an endoaortic balloon clamp being introduced via the arterial cannula. For open-heart surgery, after the balloon has been inflated (and the aorta thus clamped), all the blood is guided via the bypass.

In the prior art, a large number of balloon catheters are also known with which it is possible to close vessels in a specific manner. For example, in many cardiovascular operations, it is possible to completely close a vessel by inflating the balloon so that the latter bears against the vessel to be occluded.

However, in extracorporeal lung assist, for example, such balloon catheters are not suitable because they completely close the artery, as a result of which the flow of blood into the lower extremities or into the areas below the cannulation site is blocked, which, as has been mentioned above, may lead to ischaemia and, consequently, to ischaemic tissue necrosis.

SUMMARY OF THE INVENTION

An object underlying the invention is therefore to make available an appliance, of the type mentioned at the outset, with which blood vessels can be cannulated and which can be used also in extracorporeal lung assist without the danger of ischaemia of areas lying below the cannulation site.

According to the invention, this object is achieved by the fact that, in the appliance mentioned at the outset, at least one means is provided to permit a controlled division of the blood into a first subsidiary stream which leaves the vessel through the cannula, and a second subsidiary stream which is continued through the vessel.

The object underlying the invention is achieved completely in this way.

With the present invention, it is possible to ensure that blood guided in a vessel is not removed in its entirety from the body via a cannula, but instead only a defined proportion of the blood flowing in the vessel is removed. At the same time, means provided according to the invention ensure that another portion of the blood is continued in a controlled manner through the vessel. In this way, the supply of blood and oxygen to areas situated below the cannulation site is guaranteed.

Thus, the appliance according to the invention can be advantageously used in extracorporeal lung assist, for example, the at least one means ensuring that a controlled subsidiary stream of blood is delivered to the extracorporeal circuit and a controlled subsidiary stream of blood continues through the vessel.

The term "cannula" in the context of the present application is to be understood as meaning any appliance which can be introduced into a vessel and has a lumen. The cannula can include various materials tried and tested in medical technology, for example metals, polyurethane, etc. The cannula is preferably a wire-reinforced polyurethane cannula.

The term "means" in the context of the present invention is to be understood as any arrangement provided on the appliance and making it possible to deliberately continue part of the blood stream through the vessel.

According to one object of the appliance according to the invention, it is preferable if the subsidiary stream remaining in the vessel can be guided via the means past the cannula.

This has the advantage that not all the blood in the vessel is guided into the cannula and thus removed from the vessel. Instead, the means ensures that a subsidiary stream is deliberately guided past the cannula and into areas situated below the cannulation site. These areas can be supplied with blood and oxygen in this way.

According to another object, it is preferable if the means is a balloon which surrounds the cannula and which has a surface with at least one groove-like depression.

The term "balloon" is here to be understood as any portion on the cannula shaft having a widened diameter in relation to the cannula. The "balloon" can be applied on the outside of the cannula or can be an integral portion of the cannula.

The expression "groove-like depression" is to be understood as any change from a regular surface of the balloon making the balloon surface appear irregular, i.e. ribbed, notched, etc. In known balloon catheters, the surfaces of the balloon lie smoothly on the surface of the vessel wall, as a result of which the vessel is completely closed and a blood flow into areas below the cannulation site is prevented. In the embodiments according to the invention, the depressions on the surface advantageously allow some of the blood in the vessel to be guided also into areas situated downstream the cannulation site.

The depressions run the entire length of the balloon. Those areas of the surface lying between the depressions are raised in relation to the depressions and press against the vessel wall or the catheter. By means of the depressions in the surface of the balloon, groove-like hollows are formed through which some of the blood in the vessel can flow past the cannula into areas situated below the cannulation site.

In a preferred embodiment, the surface having at least one depression faces towards the vessel and/or the cannula.

In those embodiments in which the depressions are arranged on that surface of the balloon facing towards the vessel wall, some of the blood thus flows between vessel wall and balloon into areas situated below the cannulation site.

If the depressions are arranged on the balloon surface facing towards the cannula, some of the blood in the vessel flows between balloon and cannula past the cannulation site. The balloon is arranged on the cannula via the raised areas of its surface likewise facing the cannula. However, the depressions can also be arranged on both sides of the balloon, i.e. both on the side facing towards the vessel wall, and also on the side facing towards the cannula.

Each of these embodiments ensures that passages remain between the balloon and the vessel wall, or between balloon and cannula, or on both sides, through which passages a subsidiary stream of the blood can continue onwards through the vessel in a controlled manner to areas below the cannulation site.

The surface can in this case have at least one depression, preferably several depressions, and the flow achieved with these depressions can be controlled via their number and depth. The depressions can be of any desired shape, for example in the form of a groove or notch. The depressions can be distributed symmetrically or asymmetrically on the surface.

According to another object, the means is at least one balloon which surrounds the cannula in sections in such a way that at least two ends of the balloon pointing in the circumferential direction are located at a circumferential distance from one another.

Here, it is particularly preferable if two balloons are provided which enclose the cannula in sections.

In this embodiment, the balloon or balloons do not surround the cannula completely but instead have two ends pointing in the circumferential direction. These ends lie at a distance from one another so that, in the dilated state of the balloon, a passage is formed through which some blood is led past the cannula.

The distance between the ends of the balloon or balloons, or their section surrounding the cannula, and their arrangement on the cannula can be varied in respect of the cannula circumference and the desired amount of blood to pass through. In the dilated state, a passage is thus created through which a subsidiary stream of the blood can flow through and thus reach areas below the cannulation site.

In addition, the number of the balloons can also be varied, in each case with balloon ends situated at a circumferential distance from one another, the resulting passages being able to be set at regular or irregular intervals.

In a preferred embodiment, the balloon of the abovementioned appliances according to the invention is dilatable.

The balloon can in this case be dilated with a fluid delivered via a second lumen which is in fluidic communication with the inside of the balloon. This lumen can, for example, be guided in the form of a tube or second cannula along the outside of the first cannula or inside the latter. A saline solution, for example, can then be delivered via this tube for the purpose of dilating the balloon.

The use of a saline solution has the advantage that, if for example the balloon is damaged and the contents escape from it, no immunological reactions are triggered. When using air, for example, or other solutions, there is a danger that, if these fluids escape from the balloon into the blood, embolisms or immunological reactions may be produced and thus cause considerable damage within the human body. This danger is avoided by using physiological saline solution.

In another embodiment, it is preferable if the balloon is not dilatable. In this case, the balloon can for example be a portion of the cannula shaft which, in relation to the cannula, simply has a widened circumference.

The balloon can include a material such as latex, for example, or can be made entirely of latex. This material is sufficiently well known and established in medical technology and is, for example, a thin-walled latex material measuring 250 .mu.m in thickness.

According to another object, the subsidiary stream remaining in the vessel can be guided first into the cannula and then out of it via the at least one means.

Here, it is particularly preferable if the at least one means is an outlet in the cannula.

This has the advantage that, in the event of a narrowing of the vessel for example, all of the blood in the vessel is first guided into the cannula, but a subsidiary stream of this blood is guided back out through at least one outlet located in the cannula.

In this embodiment too, it is thus at all times guaranteed that some of the blood can be led off, and at the same time areas below the cannulation site are supplied in a defined way with blood and oxygen.

Here, it is preferable if the outlet is an opening in the cannula.

Such openings can be circular, for example, and are chosen such that a sufficient amount of blood can be guided out of the vessel and a certain amount of blood can also be led back out of the cannula and into the vessel.

The shape and size of the openings can vary according to the application, depending on how much blood is intended to reach the areas situated downstream the cannulation site. In addition, a plurality of openings can also be provided from which blood can emerge again from the cannula. In this way, it is possible to control exactly how much blood is removed from the vessel and how much blood is to be guided back into the vessel.

Moreover, according to another object it is preferable if the outlet is a tubular portion arranged on the cannula, which tubular portion is guided in the vessel.

In this embodiment, the tubular portion forks off from the cannula like a branch. In this embodiment too, it is possible, for example in the case of a narrowing of the vessel (which would normally prevent flow of blood to areas situated below the cannulation point), to deliberately divide the blood in a controlled manner into subsidiary streams. All of the blood flows first into the cannula, after which a subsidiary stream of the blood is then guided out of the vessel and another subsidiary stream is led back into the vessel via the tubular portion.

In this embodiment, which represents a kind of "cannula within a cannula", it is possible, depending on the application, to vary the length of the tubular portion, its diameter, and the angle at which it branches off from the cannula. The number of the tubular portions can also be varied.

According to still a further object, it is preferable if the outlet is a cannula-like portion on the appliance, which portion is guided at least partially outside the vessel.

In this embodiment, most of the blood in the vessel thus flows into the cannula and is led out from the vessel. A subsidiary stream of the blood can then be guided back to the cannulated vessel through a cannula-like portion lying at least partially outside the vessel.

"Cannula-like portion" in this context means an arrangement which has similar properties to a cannula or a catheter for example, i.e. can be introduced at least partially into a vessel and has a lumen. This cannula-like portion can, for example, be connected t the cannula at one end via an attachment piece. The attachment piece lies outside the vessel, so that at least that part of the cannula-like portion connected to the attachment piece is situated outside the vessel. The other end of the cannula-like portion can be introduced into the cannulated vessel, as a result of which a subsidiary stream of the blood can be guided back into the vessel.

In a refinement of the embodiments in which the subsidiary stream remaining in the vessel is first guided into the cannula and then guided back out of it via the at least one means, it is preferable if a balloon is additionally provided which is arranged on the cannula between the point of entry of the blood into the cannula and the outlet.

This embodiment has the advantage that the vessel can be closed by the balloon in such a way that all the blood conveyed in the vessel is led into the cannula, after which controlled subsidiary streams are again produced via said means.

The balloon also has the advantage that the appliance can be fixed in position in the vessel, as a result of which slipping of the appliance is avoided.

The balloon can in this case again be dilatable, for example by means of a fluid delivered via a lumen in contact with the balloon, or it can be a portion on the cannula having a widened diameter in relation to the cannula.

In a refinement of the illustrative embodiments set out above, it is preferable if means are additionally provided for measuring at least one of the subsidiary streams.

In the prior art it is known to use probes, for example, to measure the oxygen saturation in the areas below the cannulation sites. However, this measurement simply indicates whether the measured area is being supplied with fresh blood. This supply can be achieved locally via a collateral circulation, however, so that with these appliances it is not possible to measure whether a specific flow of blood is actually present in the cannulated vessel and whether the oxygen supply to all the areas below is thus guaranteed.

In a further embodiment, it is preferable if means are additionally provided for regulating the subsidiary streams.

The advantage of this is that, for example after the subsidiary stream have been measured by means provided for this purpose, these subsidiary streams can, if appropriate, be regulated. Thus, it is possible, on the one hand, to determine exactly how much blood is removed from the vessel and/or how much blood remains in the vessel. On the other hand, if necessary, the individual subsidiary streams can then be increased or reduced, for example, via regulating means.

For example, in the embodiment in which a cannula-like portion is connected via an attachment piece to the cannula outside the vessel, and in which the cannula alternately has a balloon, a measurement cell which measures the two subsidiary streams can be arranged, for example, on the attachment piece. If the subsidiary stream returned via the cannula-like portion into the vessel is below a certain level, as a result of which an adequate supply of oxygen would no longer be guaranteed, this state is detected. If appropriate, the distribution of the subsidiary streams can then be regulated by regulating means, so that less blood is removed from the vessel and thus more blood is conveyed back to the vessel.

In the other embodiments, the additional measurement device can be realized in a similar way. Thus, for example, it is possible to measure the subsidiary stream of blood in the areas below the cannulation site. It is then possible to determine to what extent it is necessary to regulate the two subsidiary streams. If a reduced subsidiary stream is measured in the cannulated vessel, this subsidiary stream can be increased for example via regulating means, for example by reducing the dilation of a balloon.

Moreover, it is generally preferable if the cannula has an external diameter of ca. 5 to 30 French, in particular of 13 to 21 French.

In one use, the external diameter of the cannula is chosen for example with regard to the vessel being cannulated. Determining the size of the cannula for each individual patient is important, because the sizes of the vessels vary greatly from patient to patient. Before the vessels are punctured, their diameter can be determined by ultrasound for example. Thus, the cannula size can be chosen optimally, for example, for the femoral artery as the critical vessel. Moreover, the diameter is determined taking into consideration the flow rate intended to be conveyed into the cannula.

Thus, in the femoral vessels, the maximum depth of insertion of the cannula is ca. 140 mm and the cannula length is for example 270 mm to 340 mm, depending on whether an introducer is used or not.

In the use of dilatable balloons too, their optimal circumference is be taken into consideration and must be determined according to the application. Thus, the balloon in the dilated state can have an external diameter of for example ca. 1 to 8 cm, in particular of 2 to 5 cm.

Here too, a different balloon size must be chosen depending on the size of the vessel intended for cannulation, and in each case the size should be sufficient to ensure that, in the dilated state, the side of the balloon facing the vessel presses firmly against the vessel wall, so that all of the blood is conveyed into the cannula.

It is further preferable if the appliance is coated with a biocompatible material.

Such a material is chosen to reduce, if not completely prevent, the risk of blood clotting and inflammatory reactions which are triggered when vessels and blood come into contact with foreign material. The appliance can be coated, for example, with the Bioline-Coating® sold by Jostra Medizintechnik, Hirrlingen, Germany. This coating is sufficiently known in the prior art and has been used successfully in medicine.

The invention as a further object relates to a method for cannulation of a blood vessel, in which method the appliance according to the invention is used.

The invention as another object further relates to a method for extracorporeal lung assist with a lung assist device, in which method the appliance according to the invention is used.

The term "lung assist device" is to be understood here as any device with which a gas exchange is possible, i.e. with which, for example, oxygen can be enriched and $CO_2$ removed, for example an oxygenator.

In this method, the femoral artery, for example, is cannulated with the appliance according to the invention, as a result of which it is possible to convey some of the blood into a lung assist device and also some of it into the areas below the cannulation site. Some of the blood is then conveyed via a tube to the lung assist device, for example to an oxygenator, is enriched with oxygen there and has $CO_2$ removed, and is delivered, for example to the femoral vein, via a further tube and a further cannula.

The appliance according to the invention is also particularly advantageous in pumpless arterio-venous lung assist. In this method, blood trauma can be minimized by omission of a blood pump and by means of a very short connection and low filling volumes. Moreover, this pumpless lung assist has the advantage that no additional machines are needed for maintaining the circulation. When appropriate cannulas are used, the patient's mean arterial pressure ensures a sufficient throughflow, the blood in the lung assist device being saturated with oxygen and having the carbon dioxide in it washed out. An important condition here is that the action of the heart is sufficient and only the pulmonary function is impaired.

The invention additionally relates to the use of the novel appliance for cannulation of a blood vessel.

The invention further relates to the use of the appliance according to the invention in extracorporeal lung assist using a lung assist device.

In this application, the appliance can be used for extracorporeal lung assist in combination with a pumpless lung assist device, for example. A lung assist device in the form of a membrane oxygenator is commercially available, for example, from the applicant, Nova Lung GmbH, Hechingen, Germany. The special feature of this heparin-coated lung assist device lies in its very low resistance with respect to a specific blood flow, for which very reason it is possible to position it between the femoral artery and the femoral vein.

With the novel appliance it is also possible to guarantee the supply of blood to areas situated below the cannulation site.

It will be appreciated that the features mentioned above and those still to be explained below can be used not only in the respectively cited combination, but also in other combinations or in isolation, without departing from the scope of the present invention.

BRIEF DESCRIPTION OF THE DRAWINGS

Embodiments of the invention are shown in the drawing and are explained in more detail in the description below. In the drawing:

FIG. 2b shows a diagrammatic cross section through the embodiment from FIG. 2a;

DETAILED DESCRIPTION OF THE PREFERRED EMBODIMENT

Figure 1:
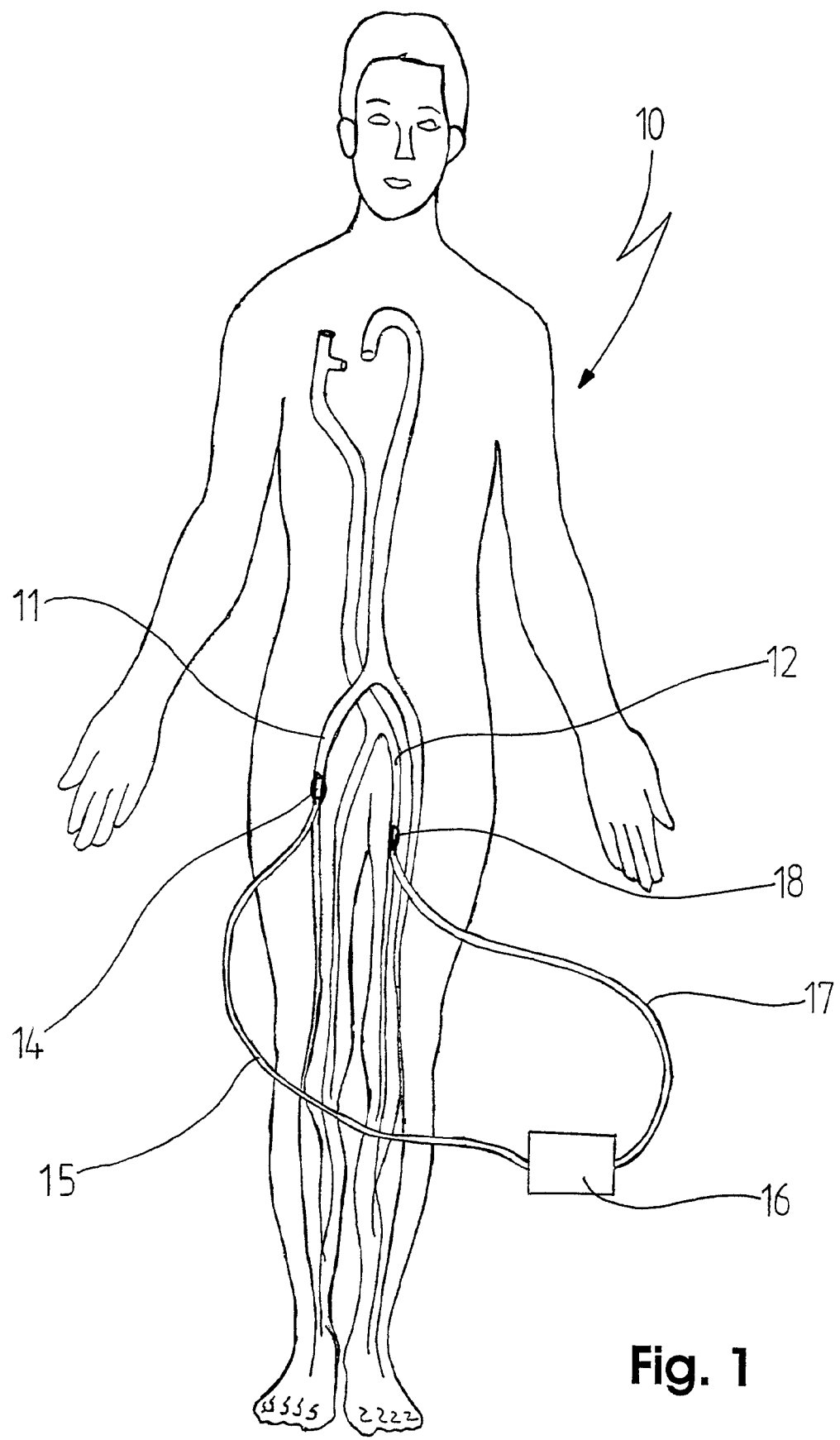
FIG. 1 shows a diagrammatic representation of the configuration of an extracorporeal lung assist on a patient.

In FIG. 1, reference number 10 designates a patient whose femoral artery is designated by 11 and whose femoral vein is designated by 12. Blood is removed from the femoral artery 11 via a cannula 14. A tube 15 leads from the cannula 14 to a lung assist device 16, and a further tube 17 leads from the lung assist device 16 to a further cannula 18 in the femoral vein 12.

FIG. 1 shows the system of extracorporeal lung assist using a femoral connection technique. Alternatively, a connection is also possible, for example, to the jugular vein via the femoral artery 11. The cannula 14 is chosen with a diameter optimally adapted to the femoral artery 11 of the patient 10 and is introduced into the femoral artery 11 as critical vessel. The patient's mean arterial pressure ensures that the blood is conveyed from the femoral artery 11 via the tube 15 to the lung assist device 16. A suitable lung assist device in the form of a membrane oxygenator is obtainable, for example, from the applicant, Nova Lung GmbH, Hechingen. By means of this lung assist device 16, the blood is enriched with oxygen and at the same time carbon dioxide is removed. The oxygen-enriched blood leaves the lung assist device 16 via the tube 17 and is delivered to the femoral vein 12 via the cannula 18.

At the point of entry of the cannula 14 into the femoral artery, some of the blood, in one use of the appliance according to the invention, can be routed past the cannula 14, or through it back into the femoral artery 11, for which reason the blood can also reach the whole of the lower leg. This circulation ensures that, in the event of weak or even absent pulmonary function, oxygen supply to all areas of the body is guaranteed.

Because of the short line length of the system, measured from cannula tip to cannula tip, there is no need to insert a heat exchanger into this lung assist. All the components can additionally be biocompatible (for example, coated with BIO-LINE-COATING®). The cannulas used are ones which are fitted percutaneously by the Seldinger technique (for example Nova Lung BE-AVC 17-01). The venous return likewise takes place via an arterial cannula since, because of its short length, it has a lower flow resistance compared to a comparable venous Seldinger cannula.

The extracorporeal lung assist can be conducted for several days to weeks (in extreme cases even for 20 to 29 days, for example).

Figure 2A:
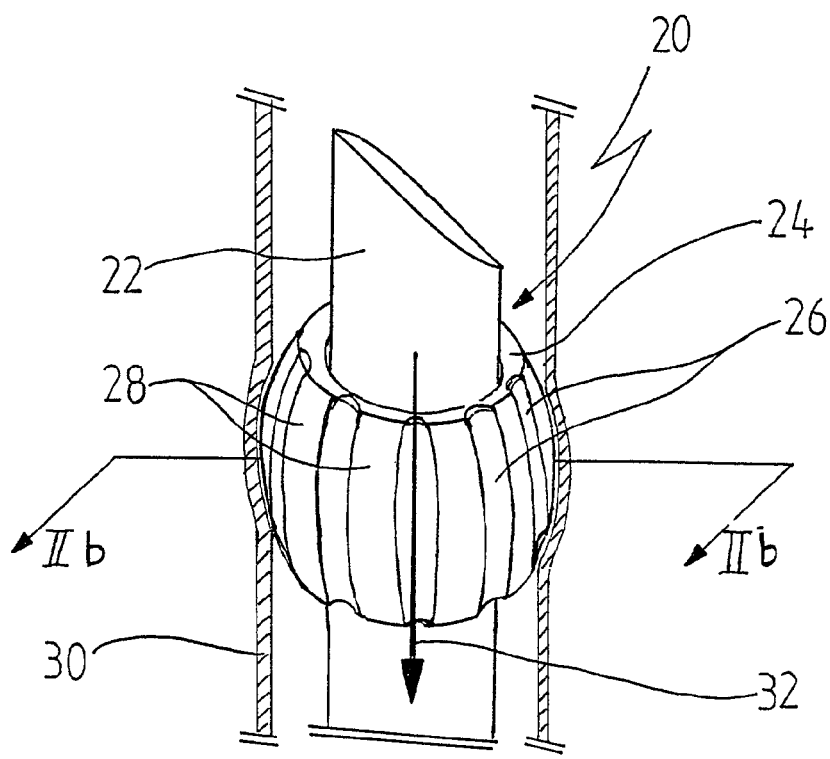
FIG. 2a shows a diagrammatic representation of an embodiment of the appliance according to the invention.
Figure 2B:
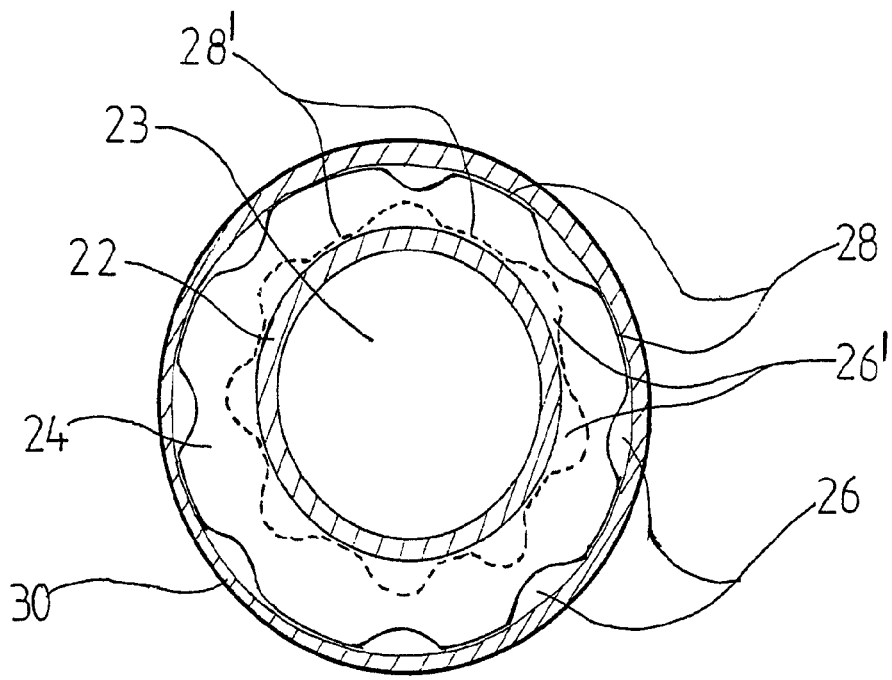
Figure 2C:
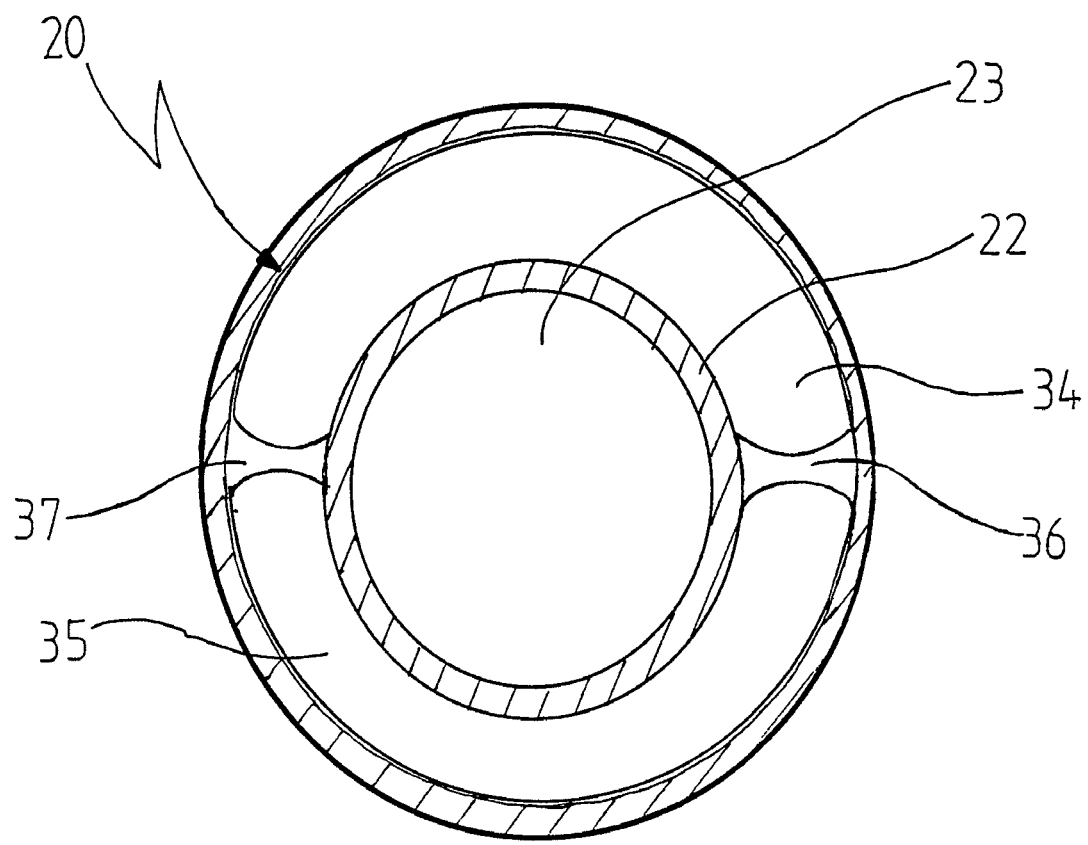
FIG. 2c shows a diagrammatic cross section through a further embodiment.

Embodiments of the appliance according to the invention are shown diagrammatically in FIGS. 2a, 2b and 2c. In these figures, similar elements are designated by the same reference numbers.

In the diagrammatic representation in FIG. 2a and in the cross-sectional representation in FIG. 2b, the appliance as a whole is designated by reference number 20. This appliance has a cannula 22 with a lumen 23 and with a balloon 24 surrounding the cannula 22. The balloon 24 in turn has passages 26 in the form of groove-like depressions which run parallel to the cannula surface or vessel and extend the full length of the surface of the balloon in the direction of the flow of blood. By means of the passages 26, raised areas 28 are formed which, as is shown in FIG. 2b, directly adjoin the wall of a vessel 30.

The number of the passages 26 on the balloon 24 can be varied as necessary, as can the depth or shape of the passages.

After introduction of the cannula 22 into a vessel 30, the balloon 24 can be dilated by means of a fluid, for example with a physiological saline solution. In the dilated state of the balloon 24, its raised areas 28 press against the wall of the vessel 30. In this way, some of the blood is forced into the lumen 23 of the cannula 22 and there forms a subsidiary stream which leaves the vessel 30 via the cannula 22. However, some of the blood can also flow past the cannula 22 via the passages 26, as a result of which a subsidiary stream is formed which continues flowing through the vessel 30, as is indicated for example by the arrow 32.

By means of the passages 26, it is therefore possible for a large part of the blood to be conveyed into the lumen 23 of the cannula 22 and outwards from the cannula 22 and, at the same time, for some of the blood to flow past the cannula 22 via the passages 26. The blood guided through the lumen 23 can be delivered to the extracorporeal blood circuit. Blood which flows past the cannula 22 via the passages 26 can reach areas below the cannulation site and can supply these areas with oxygen.

In another possible embodiment, the passages 26 on the surface of the balloon 24 can also be formed, for example, on the side facing towards the cannula 22, as passages 26'. The balloon 24 is in this case arranged on the cannula 22, for example by adhesive bonding, via the raised areas 28' which then likewise face towards the cannula 22. The surface of the balloon 24 facing the wall of the vessel 30 is then smooth and fully contiguous with the wall of the vessel 30.

It is of course also conceivable for both surfaces of the balloon 24, i.e. the surface facing towards the wall of the vessel 30 and also the surface facing towards the cannula 22, to have passages 26, 26' in the form of depressions.

Instead of a balloon with a "grooved" surface, it is also possible, for example, to provide one or more balloons which each surround the cannula in sections and whose ends are situated at a defined circumferential distance from one another. The cross section of such an embodiment is shown in FIG. 2c. In the appliance 20, two balloons 34 and 35 are arranged on the cannula 22. The ends of the balloons 34, 35 are at a distance from one another such that passages 36 and 37 are formed. Some of the blood can therefore be guided past the cannula 22 via these passages 36, 37. The distance between the ends of the balloons 34 and 35, and the arrangement of the balloons 34, 35 on the cannula, can be varied depending on the desired amount of blood that is to flow through. Thus, for example, the balloons 34, 35 can also be arranged offset on the shaft of the cannula 22.

If the balloons are dilatable, they can be dilated either via a common lumen or each via separate lumens.

Figure 3:
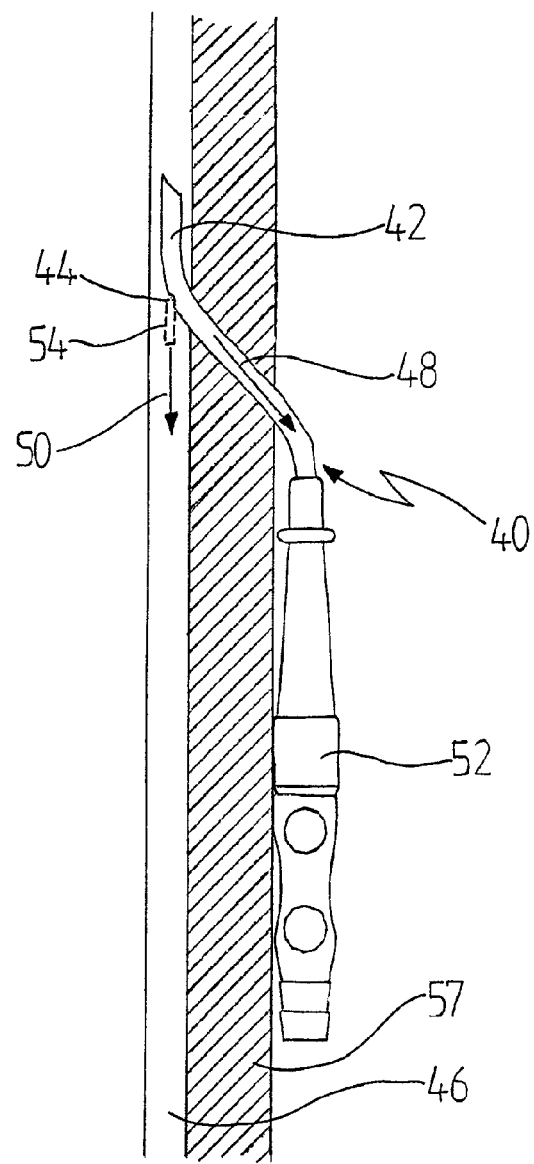
FIG. 3 shows a diagrammatic representation of a further embodiment.

In FIG. 3, an embodiment of the appliance according to the invention is indicated overall by reference number 40. The appliance 40 has a cannula 42 and also, in the cannula 42, a passage 44 in the form of a lateral outlet opening. The appliance 40 according to the invention is fitted in a vessel 46.

The cannula 42 is inserted with its distal end into the vessel 46, as a result of which most of the blood flows into the cannula. A subsidiary stream of the blood, shown by the arrow 48, leaves the vessel 46 through the cannula 42, and a subsidiary stream, shown by the arrow 50, flows through the passage 44 out of the cannula 42 and back into the vessel 46 and continues flowing through the latter. In this way, even if a vessel constriction were produced in the area of the cannula 42 during cannulation and the entire blood stream were forced into the cannula 42, it is possible to ensure that a defined subsidiary stream 50 can always leave the cannula and flow back into the vessel 46. Reference number 52 designates an attachment piece via which further arrangements and means can be fitted on the appliance, for example tubes, further cannulas, measurement cells, etc.

The broken lines in FIG. 3 also indicate another embodiment in which, instead of an outlet opening, at least one passage is formed through a tubular portion 54. As in the embodiment with the outlet opening, some of the blood can be guided back out of the cannula via this portion 54.

Figure 4:
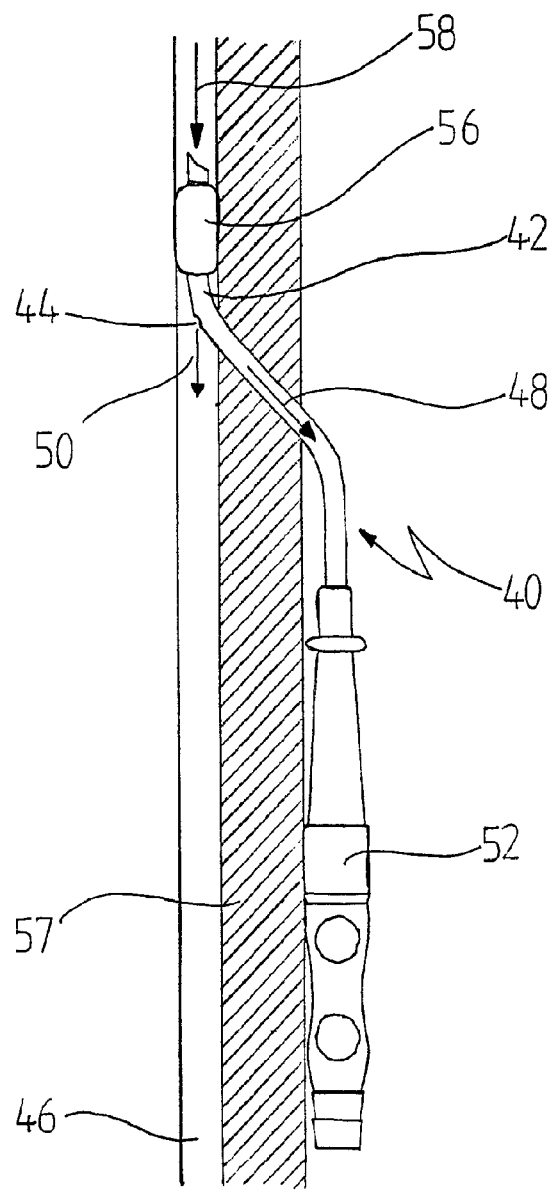
FIG. 4 shows a diagrammatic representation of a further embodiment of the appliance according to the invention.

A similar but extended embodiment is shown in FIG. 4, where the same elements are designated by the same reference numbers as in FIG. 3.

In addition to having the cannula 42 and the passage 44, the appliance 40 also has a balloon 56 which can be dilated by a fluid, for example via a lumen in the form of a thin tube guided parallel to the cannula 42. The fluid is preferably a physiological saline solution. The dilated balloon 56 presses against a vessel wall 57 via its side facing said vessel wall 57 and thus blocks the flow of blood to the areas situated below the cannulation site. In this way, all of the blood flows into the cannula 42, as is indicated by an arrow 58. The subsidiary stream 48 of the blood leaves the vessel 46 via the cannula 42, and the subsidiary stream 50 emerges from the passage 44 and continues through the vessel 46.

In this embodiment, the balloon thus functions as a kind of "spacer" keeping the cannula from the vessel wall. At the same time, the cannula 42 can be fixed in position in the vessel 46 by the dilated balloon 56.

In this way, as in the embodiment shown in FIG. 2, it is ensured that the subsidiary stream 48 of the blood in the vessel 46 can be delivered through the cannula 42 to the extracorporeal circuit, and the subsidiary stream 50 of the blood is returned into the vessel 46. With reference to FIG. 1, when using the appliance 40 according to the invention, some of the blood removed via the cannula 42 is delivered through the tube 15 to the lung assist device 16, is enriched with oxygen in the latter, and is guided back into the femoral vein via the tube 17 and the cannula 18. The other subsidiary stream 50 of blood leaves the cannula 42 via the passage 44 and thus supplies the areas below the cannulation site with blood and, consequently, oxygen.

The passage 44 can be varied in shape, size and number depending on the desired amount of blood that is to flow through.

Figure 5:
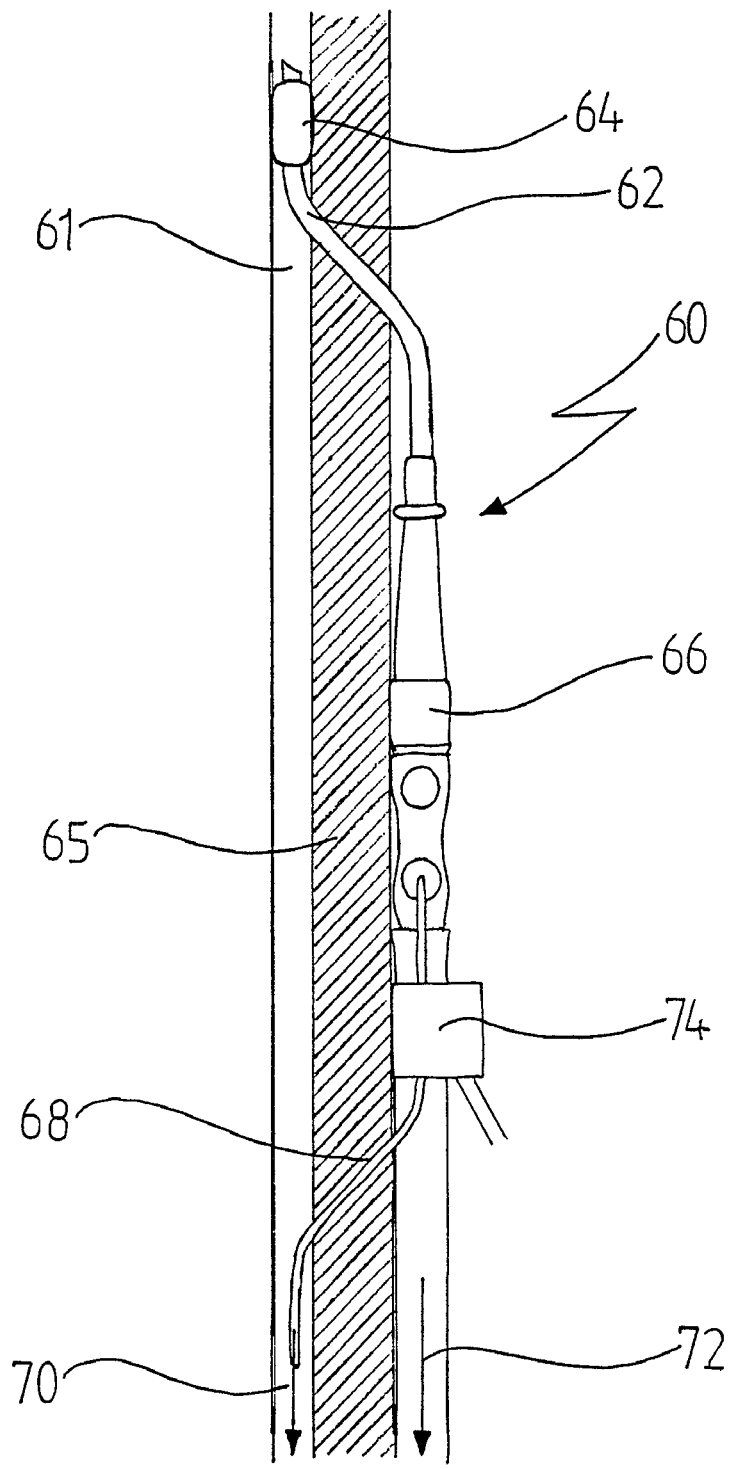
FIG. 5 shows a diagrammatic representation of a further embodiment.

FIG. 5 shows a diagrammatic representation of a further embodiment of the appliance according to the invention.

In FIG. 5, the appliance as a whole is designated by reference number 60. This appliance, lying in a vessel 61, has a cannula 62 with a balloon 64.

In the dilated state, the surface of the balloon 64 facing a vessel wall 65 presses against said vessel wall 65 and in this way forces the blood into the lumen of the cannula 62.

The blood is conveyed through a portion of the cannula 62 to an attachment piece 66 on which a cannula-like portion 68 is also arranged. A subsidiary stream can be conveyed through this cannula-like portion 68 back into the vessel 61 and thus supply the areas below the cannulation site with blood, as is indicated by an arrow 70. The arrow 72 indicates a subsidiary stream which leaves the vessel via the cannula 6.2 and the attachment piece 66. The subsidiary stream 72, which for example is delivered to a lung assist device in an extracorporeal lung assist, is preferably greater than the subsidiary stream remaining in the vessel.

In the embodiment shown in FIG. 5, a measurement cell 74 is also arranged on the attachment piece 66, with which measurement cell 74 the subsidiary streams 70 and 72 can be measured. For example, if the subsidiary stream which remains in the vessel via the cannula-like portion is disadvantageously reduced, as a result of which the supply of oxygen to the areas below the cannulation site is no longer guaranteed, this can be measured by the measurement cell 74 and can, if appropriate, be regulated. The attachment piece can, for example, include polyvinyl chloride, or it can be made entirely of this material.

The subsidiary stream flowing into the areas situated below the cannulation site can be regulated, for example, by increasing the subsidiary stream conveyed back into the vessel 61 via the cannula-like portion 68 and/or by "venting" the balloon 64 so that not all of the blood is guided into the cannula 62. Moreover, in the event of a signal indicating an inadequate supply to the lower areas, the arrangement as a whole can be removed.

In the various embodiments, the balloon is in each case arranged on the cannula by adhesive bonding. After the appliance has been introduced into a vessel, the balloon can be dilated using a fluid, for example a physiological saline solution. The fluid is in each case delivered via a second lumen which is in fluidic communication with the balloon. This lumen can extend either as a tube parallel to the cannula or can be integrated in the latter as a second lumen.

In the various embodiments, the appliance as a whole can also be coated with a biocompatible coating, for example with the BIOLINE® coating developed and sold by Jostra.

It will be appreciated that further changes and modifications are conceivable without departing from the scope of the present invention.

What is claimed is:

1. A method for establishing an extracorporeal circuit, comprising the steps of:
   a) canulating a blood vessel, with an apparatus comprising a cannula having a blood-guiding lumen, which after introduction into said vessel, said lumen is in fluid communication with said vessel, and at least one balloon surrounding said cannula;
   b) dividing in a controlled manner the blood flowing within said vessel into a first subsidiary stream which leaves said vessel through said lumen of said cannula, and a second subsidiary stream which is guided via said at least one balloon past said cannula through said vessel, wherein said balloon has a surface with at least one groove-like depression facing toward said lumen and a second surface with optionally at least one groove-like depression facing toward said vessel, and;
   c) guiding said first subsidiary blood stream through a lung assist device and then back into another blood vessel.

2. The method of claim 1, wherein the balloon is dilatable.

3. The method of claim 1, wherein the balloon is not dilatable.

4. The method of claim 1, further comprising means for measuring at least one of said subsidiary streams.

5. The method of claim 4, further comprising means for regulating said subsidiary streams.

6. The method of claim 1, further comprising means for regulating said subsidiary streams.

7. The method of claim 1, wherein said cannula has an external diameter of ca. 5 to 30 French.

8. The method of claim 1, wherein the cannula is coated with a biocompatible material.

9. The method of claim 1, wherein said blood vessel is the femoral artery.

10. A method for establishing an extracorporeal circuit, comprising the steps of:
    a) cannulating a blood vessel, with an apparatus having a cannula consisting of a single blood-guiding lumen, which after introduction into said vessel, said lumen is in fluid communication with said vessel, and at least one balloon surrounding said cannula;
    b) dividing in a controlled manner blood flowing within said vessel into a first subsidiary stream which leaves said vessel through said lumen of said cannula, and a second subsidiary stream which is guided via said at least one balloon past said cannula through said vessel, and;
    c) guiding said first subsidiary blood stream through a lung assist device and then back into another blood vessel.

11. The method of claim 10, wherein said balloon has a surface with at least one groove-like depression.

12. The method of claim 11, wherein said surface with said at least one groove-like depression faces towards said vessel and/or said cannula.

13. The method of claim 12, wherein said balloon is dilatable.

14. The method of claim 12, wherein said balloon is not dilatable.

15. The method of claim 10, wherein said balloon surrounds said cannula in sections in such a way that at least two ends of said balloon pointing in a circumferential direction are located at a circumferential distance from one another.

16. The method of claim 15, wherein two balloons surround said cannula in sections.

17. The method of claim 11, wherein said balloon is dilatable.

18. The method of claim 11, wherein said balloon is not dilatable.

19. The method of claim 10, wherein said blood vessel is the femoral artery.

20. A method for establishing an extracorporeal circuit, comprising the steps of:
    a) cannulating a blood vessel, with an apparatus having a cannula consisting of a single blood-guiding lumen, which after introduction into said vessel, said lumen is in fluid communication with said vessel, and at least one balloon surrounding said cannula;
    b) dividing in a controlled manner blood flowing within said vessel into a first subsidiary stream which leaves said vessel through said lumen of said cannula, and a second subsidiary stream which is guided via said at least one balloon past said cannula through said vessel, and;

c) guiding said first subsidiary blood stream through a lung assist device and then back into another blood vessel,
wherein said apparatus further consists of a means for measuring at least one of said subsidiary streams, a means for regulating at least one of said subsidiary streams, or combinations thereof.

21. The method of claim 20, wherein said apparatus further consists of a means for measuring at least one of said subsidiary streams and a means for regulating at least one of said subsidiary streams.

22. The method of claim 20, wherein said blood vessel is the femoral artery.

23. A method for establishing an extracorporeal circuit, comprising the steps of:
a) cannulating a blood vessel, with an apparatus comprising a cannula consisting of a single blood-guiding lumen, which after introduction into said vessel, said lumen is in fluid communication with said vessel, and at least two balloons surrounding said cannula;
b) dividing in a controlled manner blood flowing within said vessel into a first subsidiary stream which leaves said vessel through said lumen of said cannula, and a second subsidiary stream which is guided via said balloons past said cannula through said vessel, wherein said balloons surround said cannula in sections in such a way that at least two ends of said balloons pointing in a circumferential direction are located at a circumferential distance from one another and;
c) guiding said first subsidiary blood stream through a lung assist device and then back into another blood vessel.

24. The method of claim 23, wherein said balloon is dilatable.

25. The method of claim 23, wherein said balloon is not dilatable.

26. The method of claim 23, further comprising means for measuring at least one of said subsidiary streams.

27. The method of claim 26, further comprising means for regulating said subsidiary streams.

28. The method of claim 23, further comprising means for regulating said subsidiary stream.

29. The method of claim 23, wherein said cannula has an external diameter of ca. 5 to 30 French.

30. The method of claim 23, wherein said cannula is coated with a biocompatible material.

31. The method of claim 23, wherein said blood vessel is the femoral artery.

* * * * *

UNITED STATES PATENT AND TRADEMARK OFFICE
CERTIFICATE OF CORRECTION

PATENT NO.       : 8,419,671 B2
APPLICATION NO.  : 12/416847
DATED            : April 16, 2013
INVENTOR(S)      : Georg Matheis et al.

It is certified that error appears in the above-identified patent and that said Letters Patent is hereby corrected as shown below:

Title Page, Item (56):
"Office action from Cattaneo et al., U.S. Appl. No. 11/897,667, dated Mar. 9, 2009, (8 pages)." should read, --Office action from Cattaneo et al., U.S. Appl. No. 11/897,567, dated Mar. 9, 2009, (8 pages).--.

Title Page 2, Col. 1, Item (56), in Foreign Patent Documents:
"2002/0186166 A1    12/2002    Viole et al." should be removed.

Title Page 2, Col. 1, Item (56):
"DE    10006825    9/2001" should read, --DE    10008825    9/2001--.

Signed and Sealed this
Thirteenth Day of August, 2013

Teresa Stanek Rea
*Acting Director of the United States Patent and Trademark Office*